(12) United States Patent
Gruczynski et al.

(10) Patent No.: US 11,534,257 B2
(45) Date of Patent: Dec. 27, 2022

(54) LATTICE IMPACTION PAD

(71) Applicant: Howmedica Osteonics Corp., Mahwah, NJ (US)

(72) Inventors: Mark Gruczynski, Kinnelon, NJ (US); Gokce Yildirim, Weehawken, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 456 days.

(21) Appl. No.: 16/689,295

(22) Filed: Nov. 20, 2019

(65) Prior Publication Data

US 2020/0155262 A1 May 21, 2020

Related U.S. Application Data

(60) Provisional application No. 62/769,795, filed on Nov. 20, 2018.

(51) Int. Cl.
| | |
|---|---|
| *A61F 2/46* | (2006.01) |
| *A61B 90/00* | (2016.01) |
| *A61B 17/92* | (2006.01) |
| *A61B 17/00* | (2006.01) |
| *A61B 17/56* | (2006.01) |

(52) U.S. Cl.
CPC .............. *A61B 90/08* (2016.02); *A61B 17/92* (2013.01); *A61F 2/46* (2013.01); *A61B 2017/00477* (2013.01); *A61B 2017/00946* (2013.01); *A61B 2017/564* (2013.01); *A61B 2090/0807* (2016.02); *A61F 2002/4681* (2013.01)

(58) Field of Classification Search
CPC ........... A61B 90/08; A61F 2/46; A61F 2/4603
See application file for complete search history.

(56) References Cited

U.S. PATENT DOCUMENTS

| | | | |
|---|---|---|---|
| 4,863,538 A | 9/1989 | Deckard | |
| 4,944,817 A | 7/1990 | Bourell et al. | |
| 5,017,753 A | 5/1991 | Deckard | |
| 5,076,869 A | 12/1991 | Bourell et al. | |
| 5,358,525 A * | 10/1994 | Fox ........................ | A61F 2/3804 623/14.12 |
| 6,336,941 B1 | 1/2002 | Subba Rao et al. | |
| 6,679,967 B1 * | 1/2004 | Carroll, III ............... | F16F 7/12 264/516 |
| 6,875,235 B2 | 4/2005 | Ferree | |
| 6,911,045 B2 * | 6/2005 | Shimp .................... | A61F 2/4611 623/17.13 |

(Continued)

OTHER PUBLICATIONS

Page 59 of DePuySynthes / Joint Reconstruction. The base protector shown on p. 59 was on sale at least one year prior to the priority date of the application, <http://www.gsortho.org/files/attune_surgical_technique.pdf>.

*Primary Examiner* — Zade Coley
(74) *Attorney, Agent, or Firm* — Lerner, David, Littenberg, Krumholz & Mentlik, LLP

(57) ABSTRACT

In some embodiments, the present disclosure relates to a method of securing an implant into a body of a patient. Initially, the implant is placed into the body of the patient. Then, an impactor tool is used to apply a force to the implant. Subsequent to the application of force to the implant, a portion of an impaction pad on an end of the impactor tool is monitored. When the portion is observed to be deformed, the application of force onto the implant is discontinued.

11 Claims, 3 Drawing Sheets

(56) References Cited

U.S. PATENT DOCUMENTS

| | | | |
|---|---|---|---|
| 7,179,295 B2 | 2/2007 | Kovacevic | |
| 7,288,326 B2* | 10/2007 | Elzey | F16F 1/021 |
| | | | 428/179 |
| 7,491,235 B2 | 2/2009 | Fell | |
| 7,513,344 B2 | 4/2009 | Toccalino et al. | |
| 7,537,664 B2 | 5/2009 | O'Neill et al. | |
| 7,991,599 B2 | 8/2011 | Linder-Ganz et al. | |
| 8,518,121 B2 | 8/2013 | Metzger et al. | |
| 8,532,783 B2* | 9/2013 | Zimmerling | A61N 1/36038 |
| | | | 607/57 |
| 8,747,479 B2 | 6/2014 | McShane et al. | |
| 9,220,611 B2* | 12/2015 | Jones | A61F 2/4603 |
| 9,408,720 B2* | 8/2016 | Krebs | A61F 2/461 |
| 2002/0017805 A1 | 2/2002 | Carroll et al. | |
| 2003/0225414 A1* | 12/2003 | Shimp | A61F 2/4611 |
| | | | 606/99 |
| 2004/0024460 A1 | 2/2004 | Ferree | |
| 2006/0064169 A1 | 3/2006 | Ferree | |
| 2008/0004633 A1* | 1/2008 | Arata | A61B 34/20 |
| | | | 606/130 |
| 2009/0075026 A1 | 3/2009 | Vito et al. | |
| 2009/0125115 A1 | 5/2009 | Popoola et al. | |
| 2009/0275945 A1 | 11/2009 | Makower et al. | |
| 2011/0046735 A1 | 2/2011 | Metzger et al. | |
| 2013/0006370 A1 | 1/2013 | Wogoman et al. | |
| 2013/0020733 A1 | 1/2013 | Berger | |
| 2013/0071609 A1 | 3/2013 | Masse et al. | |
| 2014/0364955 A1 | 12/2014 | Smith | |
| 2015/0202048 A1 | 7/2015 | Roisin et al. | |
| 2016/0000579 A1* | 1/2016 | Ramachandran | A61F 2/461 |
| | | | 606/99 |
| 2016/0076619 A1 | 3/2016 | Cormier et al. | |
| 2016/0327113 A1* | 11/2016 | Shelley | B32B 27/12 |
| 2017/0356517 A1 | 12/2017 | Betteridge et al. | |

\* cited by examiner

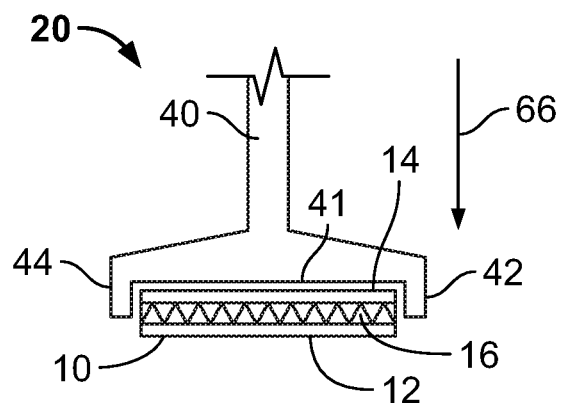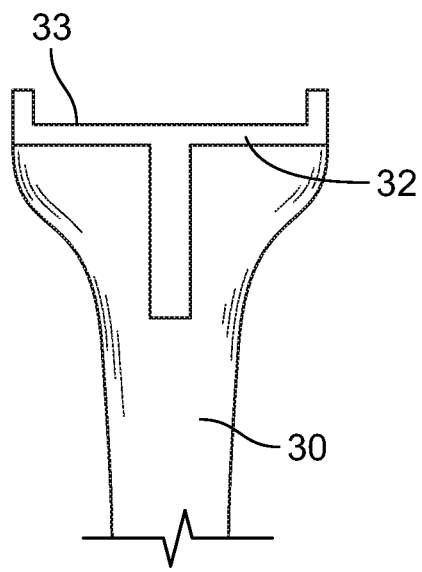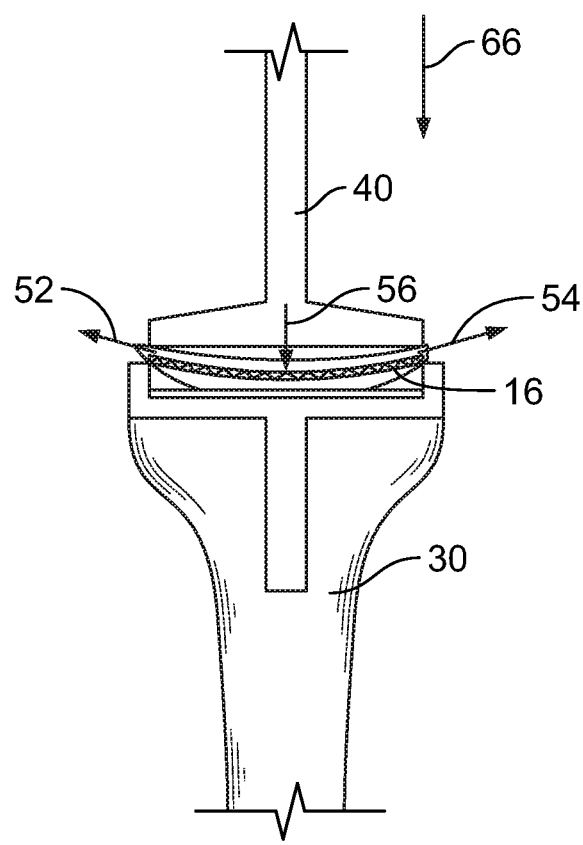
FIG. 3　　　　　　　　FIG. 4

LATTICE IMPACTION PAD

CROSS-REFERENCE TO RELATED APPLICATION

This application claims benefit of the filing date of U.S. Provisional Patent Application No. 62/769,795, filed Nov. 20, 2018, the disclosure of which is hereby incorporated by reference herein in its entirety.

BACKGROUND OF THE INVENTION

In many surgeries involving placement of an implant in the human body, impaction forces are required to be applied to the implant to fully seat it in a bone. These surgeries typically involve implants located at a joint, such as the knee, the hip or the shoulder. In such surgeries, it is often difficult for a surgeon to know whether an implant has received enough force for it to have been fully seated. This often results in unneeded force being applied to an implant. As a result, a surgical risk exists that forces applied to an implant may be unnecessarily high. Indeed, such excessive forces may lead to periprosthetic bone fractures, among other adverse outcomes.

Thus, new devices and methods are needed to monitor loads applied to an implant to ensure that the implant is properly seated.

BRIEF SUMMARY OF THE INVENTION

In some embodiments, the present disclosure relates to a device and method of use thereof that improve an ability of a surgeon to accurately seat an implant. This function is accomplished with a monolithic impaction pad that is positioned on an end of an impactor tool or on a surface of the implant to be seated. In one embodiment, the impaction pad includes three layers: An inner layer, an internal layer, and an impaction layer. Each of the inner layer and impaction layer are generally solid throughout and are separated by the internal layer. The impaction layer either directly applies or directly absorbs the impaction load while the inner layer faces a body of the tool or implant. The internal layer includes an array of geometric struts with voids in between that define a lattice. In some embodiments, the impaction pad is visually monitored while load is being applied to an implant with the tool. When deformation of the internal layer is observed, this provides an indication that a design load or other predetermined load has been successfully applied to the implant.

In one aspect, the present disclosure relates to a method of implanting an implant in the body of a patient. In one embodiment, the method includes the steps of: placing the implant in the body of the patient; monitoring a portion of an impaction pad on an end of the impactor tool or on the implant; and ceasing application of the force upon a deformation of the portion.

In some embodiments, the monitoring step includes viewing a lattice structure of the impaction pad. In other embodiments, providing the force sufficient to deform the portion of the impaction pad causes the impaction pad, connected to the impactor tool or the implant, to at least partially disconnect from the impactor tool or implant. In still further embodiments, during the providing step, the impaction pad remains connected to the impactor tool through a press fit connection between the impaction pad and the impactor tool. In some examples, providing the force causes a surface of the impaction pad facing the impactor tool or the implant to deform in a plane of the surface. In further examples, providing the force causes a lattice structure of the impaction pad to deform in a direction transverse to the plane of the surface.

In some embodiments, providing the force includes a single application of force to the implant to cause deformation of the portion of the impaction pad. In other embodiments, providing the force includes two applications of force of increasing magnitude to cause deformation of the portion of the impaction pad. In other embodiments, the method also includes a step of attaching the impaction pad to the impactor tool or the implant.

In one embodiment, the present disclosure relates to a method of determining whether a predetermined force is applied to an orthopedic implant, the method including a step of providing a predetermined force to an orthopedic implant with an impactor tool having an impaction pad connected thereto, the impaction pad having a porous portion. In the method, the application of the predetermined force causes a deformation in shape of the porous portion of the impaction pad.

In some embodiments, the application of the predetermined force causes an outer portion of the impaction pad to deform in a direction transverse to the deformation of the porous layer. In other embodiments, the application of the predetermined force causes the porous portion of the impaction pad to plastically deform. In still further embodiments, the providing step further includes at least two applications of force to the orthopedic implant to cause the portion of the impaction pad to deform.

In another aspect, the present disclosure relates to a system that includes an impactor tool and an impaction pad. The impactor tool has an end with an engagement feature. The impaction pad is connected to the engagement feature and includes an impaction surface, an inner surface facing the impactor tool, and an internal layer with a porous structure positioned in between the impaction surface and the inner surface. When the impaction pad of the system is subject to a predetermined force, the impaction pad deforms.

In other embodiments, the porous structure of the impaction pad plastically deforms when subject to the predetermined force. In further embodiments, when the predetermined force is applied to the impaction pad, the deformation includes an expansion of a perimeter of the inner surface such that the perimeter of the inner surface disengages from the engagement feature. In some examples, the porous structure of the impaction pad deforms in a direction transverse to a direction of the expansion of the perimeter of the inner surface.

In some embodiments, the porous structure is a lattice structure and includes an array of overlapping geometric struts of material. In other examples, the array of overlapping geometric struts of material are arranged in a pattern. In still further examples, the impaction pad is made of a polymeric material.

BRIEF DESCRIPTION OF THE DRAWINGS

The present disclosure will be better understood on reading the following detailed description of non-limiting embodiments thereof, and on examining the accompanying drawings, in which:

FIGS. 3-4 depict steps performed in a method of seating an implant according to one embodiment of the disclosure.

DETAILED DESCRIPTION

The present disclosure relates to an impact absorbing pad adapted for monitoring forces applied to an implant by an impactor tool and indicating when a predetermined load has been applied to the implant. In the embodiments described herein, the impaction pad is described for use to seat a tibial implant. However, such exemplary application is by no means limiting, and it is contemplated that the impaction pad may be used to monitor impaction loads for any number of implants requiring the provision of impaction loads to fully seat the implant, such as implants in a hip or shoulder joint, for example.

Figure 1:
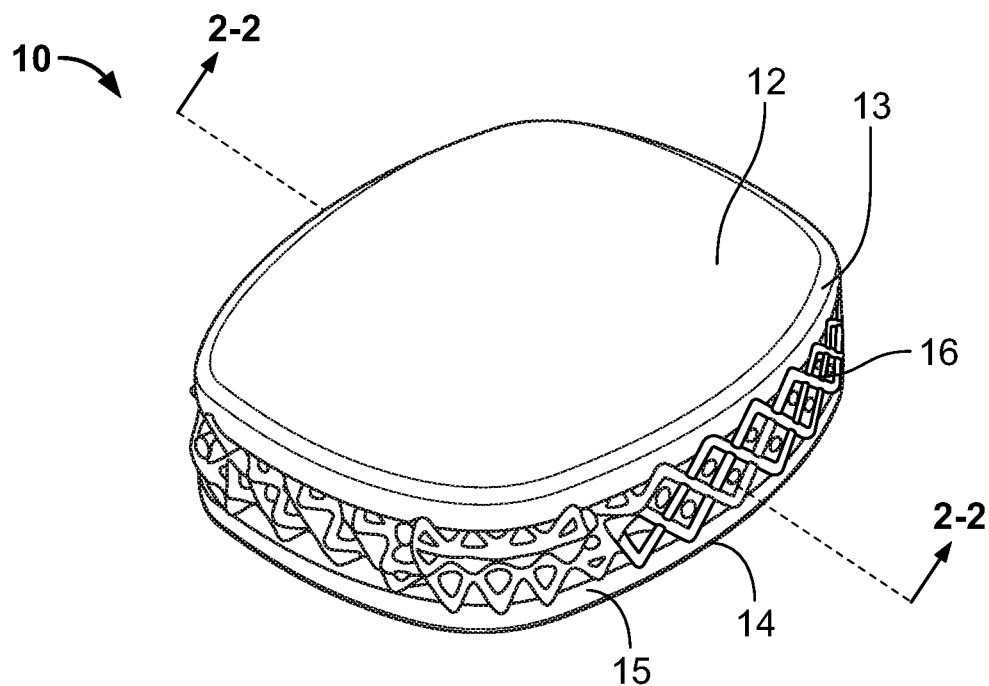
FIG. 1 is a perspective view of an impaction pad according to one embodiment of the disclosure.
Figure 2:
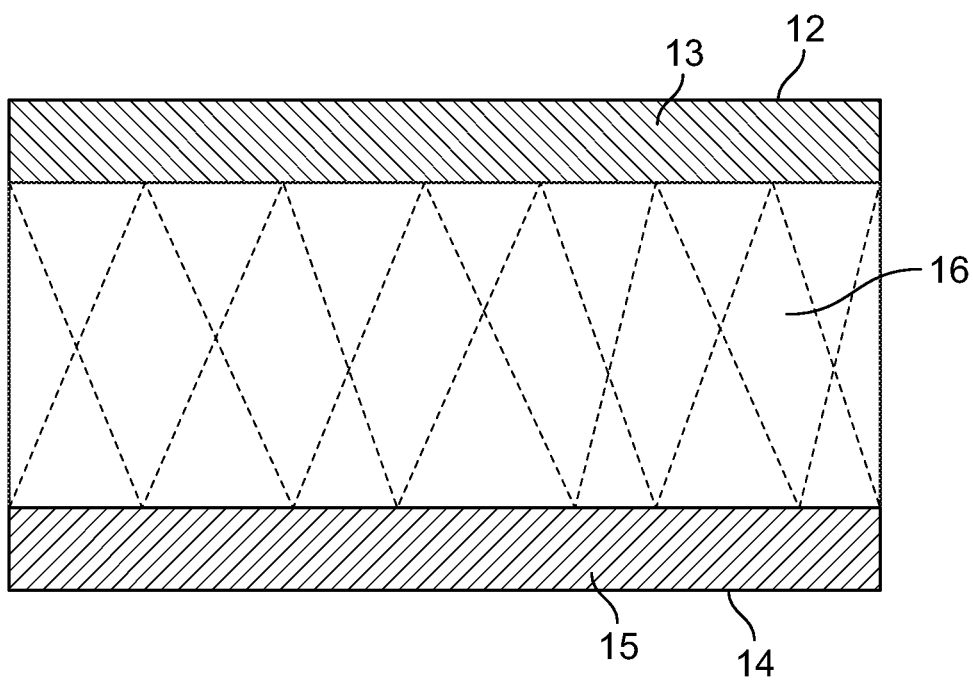
FIG. 2 is a cross-sectional view of the impaction pad of FIG. 1.

In one aspect, the present disclosure relates to an impaction pad structure. One embodiment of impaction pad 10 is shown in FIGS. 1 and 2 and includes an inner layer 15, an internal layer 16 and an impaction layer 13. Each layer has a similar perimeter, although it is contemplated to have layers of differently shaped perimeters. As shown in FIGS. 1 and 2, each of inner layer 15 and impaction layer 13 are generally solid throughout while internal layer 16 forms a lattice structure. Internal layer 16 is thicker than each of impaction layer 13 and inner layer 15, although the different thicknesses can vary. As shown in FIG. 1, the lattice structure is comprised of an array of geometric struts of material, many at angles with respect to the others, and overlapping with one another within internal layer 16. Voids occupy spaces between the geometric struts. In this manner, internal layer 16 is porous. FIG. 2 illustrates a section through impaction pad 10 where the lattice is also visible. It should be appreciated that the lattice is three dimensional and extends throughout a volume within the perimeter of the impaction pad, including through the section shown in FIG. 2. Although internal layer 16 has been described with specific characteristics, it is also contemplated that arrangements of the geometric struts may vary, and further examples are provided below. Impaction pad 10 is generally rectangular in shape with rounded corners to suit placement on an end of an impactor tool or within an implant, such as a tibial implant. Of course, in other examples, a shape of the impaction pad may vary to suit a desired application. Surfaces 12, 14 of impaction pad 10 are generally flat, as shown in FIGS. 1 and 2, although it is contemplated that these surfaces may have an irregular, curved, angular or other non-planar surface. Such variation may be guided by the intended application of the impaction pad. For example, a pad for use with a femoral implant may be contoured to a shape of such implant while a pad for a tibial base plate may be flat on its outer surface.

As depicted, impaction pad 10 is a monolithic structure and is not comprised of separate parts that are attached to one another. Further, impaction pad 10 is formed from polymeric materials, though other materials may also be used. Polymeric materials are advantageous in that when the impaction pad deforms, any debris broken off from the deformed structure is less likely to have an adverse impact on the implant site and surrounding anatomy compared to other materials, such as certain metals.

The impaction pad may be varied in many ways. For instance, a shape of the impaction pad may be customized to suit an area of a particular impaction head on an impactor tool, or a surface of an implant to be implanted in a patient. Further, customization for an implant may be for an implant used in a particular joint in a body. For example, the pad may be elliptical or one of a variety of polygonal shapes, or it may have a combination of shapes distinguishable by layer. In many examples, in an undeformed state, the internal layer will be thicker than each of the impaction layer and the inner layer. However, the ratio between thicknesses of each layer may vary to suit surgical conditions. Also, it is possible that the internal layer may indeed be thinner than one of the impaction layer or inner layer in some applications, such as those where there is very little space to position the impactor pad for use in seating an implant. In the same manner that a thickness of each layer of the impaction pad may vary, so too may the width. In one example, the internal layer has a larger area defined by its perimeter than either of the impaction layer or the inner layer when the impaction pad is in an undeformed state. In another example, the inner surface of the impaction pad has a larger area defined by its perimeter than the impaction surface.

The impaction pad may also be modified to include protrusions, recesses or other surface features to improve engagement with a tool, such as an impactor, or an implant. In some examples, the impactor includes engagement features that provide for a snug fit of the impaction pad. In others, the engagement features provide for a press fit or a friction fit. In such a snug or press fit configuration, the dimensions and materials may be chosen to obtain a desired performance when the pad is engaged to a tool or an implant. In an example of a friction fit configuration, side surfaces of the impaction pad may be roughened to contact corresponding roughened surfaces on an impactor tool.

In further examples, the internal layer may be a lattice structure that includes geometric struts of material that form a partial pattern or a pattern throughout the internal layer. In some examples, the struts are randomly arranged. In still further examples, the impaction pad includes more than one internal layer, each having a different arrangement of geometric struts. For example, two internal layers may include one layer with a random arrangement of struts having a first density and a second layer with a random arrangement of struts having a second density. In another example, one layer may have a random arrangement of geometric struts while another layer may have a patterned arrangement of geometric struts. It is contemplated that impaction pads with multiple internal layers may include any number and combination of strut structures that are random and/or patterned. In still further examples, the internal layer is not strictly limited to a lattice structure, and may have a honeycomb structure or other arrangement of struts that forms a porous layer within the impaction pad structure. In still further examples, the impaction pad may have two or more components so that it is not monolithic.

In some examples, the impaction pad may be manufactured for single use so that it is dispensable. One advantage of single use impaction pads is that such pads do not require repeated sterilization and cleaning. Alternatively, the impaction pad may be recycled after use to form an entirely new impaction pad from the same material. This is a practical option particularly when additive manufacturing is the process adopted to manufacture the impaction pad. Manufacture of the impaction pad via additive manufacturing is described in greater detail below.

In another aspect, the present disclosure relates to a system for applying a predetermined amount of force on an implant. In one embodiment, as shown in FIGS. 3-4, an implant seating system 20 includes an impactor tool 40 and impaction pad 10. Impactor tool 40 includes engagement features in the form of edge projections 42, 44 on opposite sides of an end face 41 of impactor tool 40. Of course, the engagement features may vary in view of the impactor tool included. As shown in FIG. 3, impaction pad 10 is positionable in between edge projections 42, 44 and has a undeformed dimension slightly larger than a space between the edge projections so that once positioned in between the edge projections, impaction pad 10 remains connected to the tool via a press fit. As shown in FIG. 3, inner surface 14 of impaction pad 10 is positioned against end face 41 of impactor tool 40. The combination of the impactor tool and impaction pad is such that the pair remain engaged until the predetermined force is applied to the pad and deformation occurs in the pad as it is subject to such force. This is described in greater detail below in conjunction with the methods of use of the impaction pad.

Figures 5, 6:
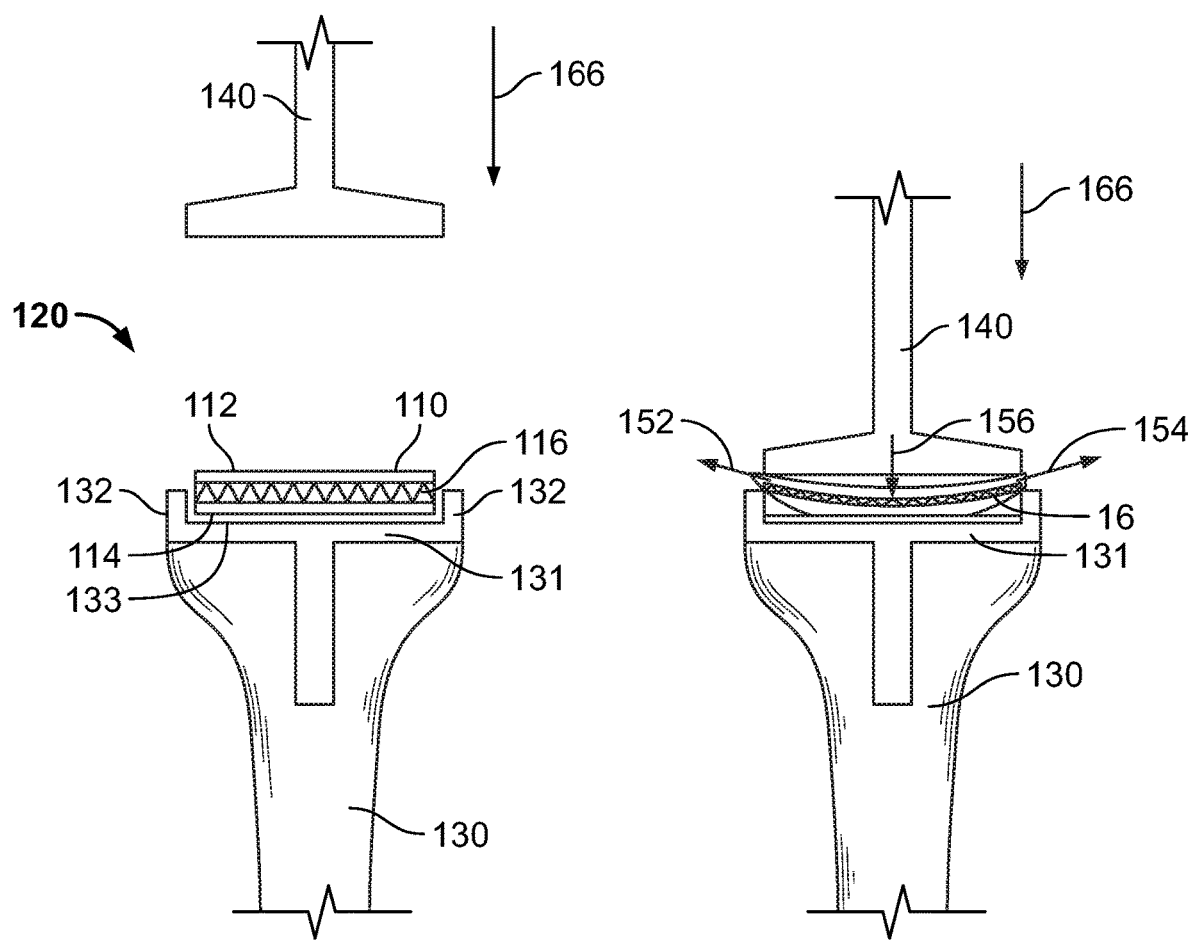
FIGS. 5-6 depict steps performed in a method of seating an implant according to another embodiment of the disclosure.

In another embodiment, a system 120 includes impaction pad 110 and a tibial implant 131. As shown in FIG. 5, tibial implant 131 includes an edge projection 132 that encloses a perimeter of implant surface 133. In a manner similar to implant seating system 20, impaction pad 110 is sized to engage with tibial implant 131 when positioned within the bounds of edge projection 132. Impaction pad 110 is oriented so that inner surface 114 faces implant surface 133 and impaction surface 112 faces away from the implant.

The system may be varied in many ways. Engagement features on one or both of the impactor tool and the impaction pad may be any known to those of skill in the art, and may vary based on the particular impactor tool employed for a given surgery. In some examples, the impactor tool and impaction pad may be integral. In those examples, the impactor tool is disposed of after use if the pad is configured to undergo plastic deformation when subject to a predetermined impact force. In some instances, it may be reusable, such as when the impaction pad is configured to undergo elastic deformation. In systems that involve a combination of an impaction pad and implant, the implant may be any implant that is seated in a patient through a procedure involving application of an impaction force, and further, because implants may have various shapes, the corresponding impaction pad may vary in size and shape to match the implant. Examples include a variety of orthopedic implants such as implants in the knee, as described above, a glenoid head in a reverse shoulder or an acetabular head in a reverse hip. The impaction pad is particularly well adapted for use in the knee as it may be difficult to visualize proper seating of a tibial implant from behind the knee when accessed from the front.

In another aspect, an impaction pad may be included with a combination of one or more additional impaction pads, one or more impactor tools, and/or one or more implants as a kit. In one embodiment, a kit includes two impaction pads, each having a different size. In another embodiment, a kit includes two impaction pads, each having a different shape. In another embodiment, a kit includes a group of impaction pads that are all the same. In yet another embodiment, a kit includes a first set of impaction pads that are all the same along with a second set of impaction pads different from the first set. It should be appreciated that the above embodiments are illustrative and that any combination of the above embodiments may be used to form a kit.

In some embodiments, a kit includes an impaction pad and an impactor tool. Any number and variety of impactor tools may be included with an impaction pad in a kit, and any combination of impaction pads such as those described in the embodiments above may be included in a kit with one or more impactor tools. In these embodiments, one or more implants may also be added to the kit or one or more implants may be substituted for an impactor tool.

The kit may be varied in many ways. For example, the various combinations of elements of any contemplated kit may be included in a single package or distributed among multiple packages. In other examples, the kit contemplated herein may be accompanied by an instruction manual on how to perform one or more of the methods of using the contents of the kit.

In another aspect, the present disclosure relates to a method of manufacturing an impaction pad, such as impaction pad 10. In one embodiment, a monolithic impaction pad is formed through additive layer manufacturing (ALM) techniques that are known to produce high resolution and dimensionally accurate articles. For example, when plastic materials are used, fused filament fabrication (FFF) or Plastic Jet Printing (PJP) may be employed, where strands of molten material are extruded from a nozzle to form layers onto a substrate in which the material hardens upon extrusion. In another example using digital light processing (DLP), photosensitive resin plastic is cured by light and built layer by layer from the bottom-up or a vat of liquid polymer is exposed to balanced levels of ultraviolet light and oxygen to produce a part often from the top-down. In three-dimensional inkjet 3D printing, a liquid binding material is selectively deposited across a thin layer of a powder and the process is repeated in which each new layer is adhered to the previous layer. Other techniques may also be employed, such as stereolithography and selective laser sintering (SLS). Detailed descriptions of the SLS technology may be found in U.S. Pat. Nos. 4,863,538, 5,017,753, 5,076,869, and 4,944,817, the entire disclosures of which are incorporated by reference herein.

When metal materials are used, other additive manufacturing techniques may also be employed, including electron beam melting (EBM), selective laser melting (SLM) and blown powder fusion. A detailed description of the use of SLM technology may be found in U.S. Pat. No. 7,537,664, the entire disclosure of which is incorporated by reference herein.

In another aspect, the present disclosure relates to a method of using an impaction pad to control a force provided to an implant with an impactor tool. In one embodiment, implant seating system 20, including impactor tool 40 and impaction pad 10, is as shown in FIG. 3 ready for use in seating an implant. Also in FIG. 3, tibial implant 32 is positioned over a tibia 30 and ready for seating. To seat the implant, impactor tool 40 is lined up over the implant, and then swung, as indicated by reference numeral 66, onto an implant surface 33 to apply a force. After the first application of force onto the implant, internal layer 16 of impaction pad 10 is visually observed to determine whether it has undergone any deformation. For purposes of this procedure, any relevant deformation will be visible to the human eye. If internal layer 16 has deformed, such as is shown in FIG. 4 where it has expanded laterally 52, 54, i.e., parallel to a plane through the impaction surface, and compressed in a direction 56 transverse, e.g., perpendicular, to the impaction surface, then this indicates that a predetermined force has been successfully applied to tibial implant 32 that is sufficient to indicate that the implant is seated and that no further applications of force with impactor tool 40 are required. The predetermined force may be a design load for the implant being seated. Of course, the exact direction of lateral expansion and transverse compression of the impaction pad may vary as a function of whether the impactor tool strikes the implant directly or at an offset and as a function of the properties of the impaction pad itself, among other factors.

When deformation of the lattice structure in internal layer 16 is visible, inner layer 15 is correspondingly deformed, i.e., expanded laterally in a direction transverse to the deformation of the lattice structure. As noted elsewhere in the disclosure, this lateral expansion partially disconnects the impaction pad from the impactor tool making the impaction pad easily removable from within edge projections 42, 44 of the tool. This eases the process of replacing the impaction pad on the tool so that the tool is ready for use on another implant. It should be appreciated that deformation of internal layer 16 of impaction pad 10 is plastic deformation, and as such, is advantageous in that the deformation remains observable even after a period of time lapses following application of a force sufficient to cause deformation. It is also contemplated, however, that the impaction pad may be designed so that the internal layer, but not the internal or impaction layers, deforms when subject to an impact force.

If there is no visible deformation after the tool is swung onto the implant to provide the first application of force, the same process is repeated a second time with a magnitude of force greater than that applied initially. Until visible deformation is observed in internal layer 16 of impaction pad 10, this process is repeated while the impaction pad continues to be visually monitored.

In another embodiment, the same method as described above and shown in FIGS. 3 and 4 is performed with impactor tool 140 and system 120, as shown in FIGS. 5 and 6. Unless otherwise indicated, like reference numerals refer to like elements shown in FIGS. 3 and 4. With impact seating system 120, tool 40 is swung, as shown by reference numeral 166, onto impaction pad 110 until deformation of pad 110 is visually perceptible. Upon deformation, pad 110 is easily removable from tibial implant 131.

In other embodiments, the method may be performed with any system described herein, having any combination of features between an impaction pad and an impactor tool or implant for engagement between the two. In further embodiments, one or more sensors may be attached to the impaction pad so that a signal may be sent when a predetermined load has been applied to the pad. In variants, the sensor may be configured to send a signal in response to a force lower than the predetermined force.

A method of seating an implant using the impaction pad is advantageous for many reasons. For example, a risk of applying too much force to an implant and damaging bone structure is drastically reduced through the visual indication provided by the impaction pad. Moreover, the pad is simple and easy to use as part of a surgical procedure. One reason for this is because the inclusion of the impaction pad does not require any specialized instruction for proper use. The method may also be applied to a wide variety of anatomical locations because the impaction pad may be made into a customized shape based on formation through additive manufacturing.

Although the disclosure herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present disclosure as defined by the appended claims.

The invention claimed is:

1. A method of implanting an implant in a body of a patient comprising the steps of:
   placing the implant in the body of the patient;
   providing a force to the implant with an impactor tool;
   monitoring a lattice structure portion of an impaction pad on an end of the impactor tool; and
   ceasing application of the force upon a plastic deformation of the lattice structure portion,
   wherein the plastic deformation indicates that a predetermined force has been applied by the impactor tool.

2. The method of claim 1, wherein providing the force sufficient to plastically deform the lattice structure portion of the impaction pad causes the impaction pad, connected to the impactor tool, to at least partially disconnect from the impactor tool.

3. The method of claim 1, wherein during the providing step, the impaction pad remains connected to the impactor tool through a press fit connection between the impaction pad and the impactor tool.

4. The method of claim 3, wherein providing the force causes a surface of the impaction pad facing the impactor tool or the implant to deform in a plane of the surface.

5. The method of claim 4, wherein providing the force causes the lattice structure portion of the impaction pad to deform in a direction transverse to the plane of the surface.

6. The method of claim 1, wherein providing the force includes a single application of force to the implant to cause plastic deformation of the lattice structure portion of the impaction pad.

7. The method of claim 1, wherein providing the force includes two applications of force of increasing magnitude to cause plastic deformation of the lattice structure portion of the impaction pad.

8. The method of claim 1, further comprising attachment of the impaction pad to the impactor tool.

9. A method of determining whether a predetermined force is applied to an orthopedic implant comprising:
   providing a predetermined force to an orthopedic implant with an impactor tool having an impaction pad connected thereto, the impaction pad having a porous portion defined by a lattice structure,
   wherein the application of the predetermined force causes a plastic deformation in shape of the porous portion of the impaction pad, the plastic deformation indicating that the predetermined force has been applied to the orthopedic implant.

10. The method of claim 9, wherein the application of the predetermined force causes an outer portion of the impaction pad to deform in a direction transverse to a direction of deformation of the porous layer.

11. The method of claim 9, wherein the providing step further comprises at least two applications of force to the orthopedic implant to cause the porous portion of the impaction pad to plastically deform.

* * * * *